(12) United States Patent
Suhr et al.

(10) Patent No.: US 11,346,828 B2
(45) Date of Patent: May 31, 2022

(54) MEASURING ARRANGEMENT FOR OPTICALLY MEASURING MILK DURING MILKING

(71) Applicant: GEA Farm Technologies GmbH, Bönen (DE)

(72) Inventors: Olaf Suhr, Oelde (DE); Adib Matty, Essen (DE)

(73) Assignee: GEA FARM TECHNOLOGIES GMBH, Bönen (DE)

( * ) Notice: Subject to any disclaimer, the term of this patent is extended or adjusted under 35 U.S.C. 154(b) by 0 days.

(21) Appl. No.: 17/052,027

(22) PCT Filed: May 9, 2019

(86) PCT No.: PCT/EP2019/061919
§ 371 (c)(1),
(2) Date: Oct. 30, 2020

(87) PCT Pub. No.: WO2019/219497
PCT Pub. Date: Nov. 21, 2019

(65) Prior Publication Data
US 2021/0239671 A1 Aug. 5, 2021

(30) Foreign Application Priority Data
May 15, 2018 (DE) ............... 10 2018 111 675.6

(51) Int. Cl.
*G01J 3/46* (2006.01)
*G01N 33/04* (2006.01)
(Continued)

(52) U.S. Cl.
CPC ............ *G01N 33/04* (2013.01); *G01N 21/05* (2013.01); *G01N 21/31* (2013.01); *G01N 21/85* (2013.01); *G01N 2021/0389* (2013.01)

(58) Field of Classification Search
CPC ........ G01J 3/46; G01J 3/50; G01J 3/02; G01J 3/524; G01J 3/51
(Continued)

(56) References Cited

U.S. PATENT DOCUMENTS 3,757,773 A 9/1973 Kolin
4,019,385 A 4/1977 Watanabe
(Continued)

FOREIGN PATENT DOCUMENTS

CN 110291315 A 9/2019
DE 3020161 A1 12/1981
(Continued)

OTHER PUBLICATIONS

International Search Report for PCT Application No. PCT/EP2019/061919 dated May 9, 2019, 10 pages.
(Continued)

*Primary Examiner* — Md M Rahman
(74) *Attorney, Agent, or Firm* — Patent Portfolio Builders PLLC

(57) ABSTRACT

An optical milk measuring arrangement operative during a milking operation, and including an optical measuring device for measuring optical properties of milk in a measuring region, in which at least part of the milk fed to the measuring arrangement collects. The measuring arrangement includes a main channel and a measuring channel, and these channels are in fluid communication with one another in a region of a common inlet and a common outlet, and the measuring channel has a lower flow velocity than a flow velocity in the main channel.

24 Claims, 6 Drawing Sheets

(51) Int. Cl.
*G01N 21/05* (2006.01)
*G01N 21/31* (2006.01)
*G01N 21/85* (2006.01)
*G01N 21/03* (2006.01)

(58) Field of Classification Search
USPC .......................................................... 356/402
See application file for complete search history.

(56) References Cited

U.S. PATENT DOCUMENTS

| | | |
|---|---|---|
| 4,372,249 A | 2/1983 | Kiestra et al. |
| 4,480,484 A | 11/1984 | Ueyama |
| 5,038,621 A | 8/1991 | Stupecky |
| 5,094,112 A | 3/1992 | Hoefelmayr et al. |
| 5,245,946 A | 9/1993 | Hoefelmayr et al. |
| 5,247,836 A | 9/1993 | Lew et al. |
| 5,503,026 A | 4/1996 | Böhm et al. |
| 5,568,788 A | 10/1996 | van den Berg et al. |
| 5,704,311 A | 1/1998 | van den Berg et al. |
| 6,297,505 B1 | 10/2001 | Frandsen et al. |
| 6,823,817 B2 | 11/2004 | van den Berg et al. |
| 7,409,871 B2 | 8/2008 | Wang et al. |
| 7,992,450 B2 | 8/2011 | Springer et al. |
| 2009/0025484 A1* | 1/2009 | Springer .................. G01F 1/56 73/861.08 |
| 2010/0273273 A1 | 10/2010 | Cross et al. |
| 2015/0146194 A1 | 5/2015 | Schönrock et al. |
| 2017/0086421 A1 | 3/2017 | Van Halsema et al. |
| 2020/0080650 A1 | 3/2020 | Williams |

FOREIGN PATENT DOCUMENTS

| | | |
|---|---|---|
| DE | 3737607 A1 | 5/1989 |
| DE | 3935759 A1 | 5/1991 |
| DE | 69715024 T2 | 1/2003 |
| DE | 10319467 B3 | 7/2004 |
| DE | 102018111675 | 6/2018 |
| EP | 0498080 A2 | 8/1992 |
| EP | 0536080 A2 | 4/1993 |
| EP | 3555507 | 10/2019 |
| GB | 2342167 | 4/2000 |
| IL | 266954 | 7/2019 |
| IN | 201917023551 | 8/2019 |
| WO | 9631764 A1 | 10/1996 |
| WO | 99/45344 | 9/1999 |
| WO | 0013011 A1 | 3/2000 |
| WO | 03040704 A1 | 5/2003 |
| WO | 03098192 A1 | 11/2003 |
| WO | 2018111675 A1 | 6/2018 |
| WO | 2019219497 A1 | 11/2019 |

OTHER PUBLICATIONS

International Search Report for PCT Application No. PCT/EP2019/061919 dated Oct. 7, 2019, 2 pages.

Office Action for U.S. Appl. No. 11/663,414 dated Dec. 28, 2009.

* cited by examiner

MEASURING ARRANGEMENT FOR OPTICALLY MEASURING MILK DURING MILKING

CROSS REFERENCE TO RELATED APPLICATION

This application is a national phase application under 35 U.S.C. 371 of PCT Application No. PCT/EP2019/061919 filed May 9, 2019, which claims priority to German Application No. 10 2018 111 675.6 filed May 15, 2018, the disclosures of which are incorporated by reference herein.

FIELD AND BACKGROUND OF THE INVENTION

The invention relates to a measuring arrangement for optical measurements on milk during a milking process, comprising an optical measuring device for measuring optical properties of the milk in a measurement region, in which at least a portion of the milk fed to the measuring arrangement collects.

Optical measurements, in particular transmission and/or reflection measurements in the visible (VIS—visible) to the near infrared (NIR—near infrared) spectral range, represent a measurement method which is fast and which can therefore be carried out in situ during a milking process in order to determine the composition of milk. By way of example, a fat content, protein content, lactose content and/or urea content can be determined for feed control purposes. The colour of the milk can also be determined, making it possible to deduce a blood content in the milk and thus any diseases that are present. In addition, an SCC value (somatic cell count) can be determined at least approximately, which can indicate inflammation in the region of the udders and teats of a milk-producing animal based on the milk that has been milked. In milk-producing animals, it is important to identify such inflammations, for example mastitis, in order on the one hand to be able to treat the animals as quickly as possible and on the other hand to exclude from further processing any milk that has a high cell content.

An inline measuring cell for optical measurements, which can be inserted in the flow of a milk line, is known from document WO 03/040704 A1. In said measuring cell, a channel that leads through the measuring cell widens downwards in a trough-like manner in the central region of the measuring cell. A measurement window for the optical measurement is arranged approximately in the central region of the trough-like widening. The downwardly pointing trough-like widening is not necessarily formed over the entire cross-sectional width of the line, but rather is preferably narrower in order to enable a transmitted-light measurement.

Document US 2010/0273273 A1 describes a similar set-up, with a drainage opening additionally being arranged in the lower region of the trough-like widening in order to be able to empty and also to flush said measurement region.

In both cases, however, the inflow of milk into the measuring cell can lead to very noisy measurements and/or measurements with significantly varying measured values. This can be observed in particular when very foamy milk flows in.

SUMMARY OF THE INVENTION

The present invention provides a measuring arrangement by which optical measurements can be carried out during the milking process with the measured values varying as little as possible and with a low noise component.

A measuring arrangement according to the invention is characterized in that a main channel and a measurement channel are formed, which channels are hydraulically connected to one another in the region of a common inlet and a common outlet, wherein a lower flow velocity prevails in the measurement channel than in the main channel, and wherein the measurement region is formed in the measurement channel.

The milk stream is thus split into a main stream and a measurement stream, it being possible for the flow velocity of the measurement stream to be reduced so that a measurement can be carried out as free of disruption as possible and in particular without any turbulent flow and with as few air bubbles as possible. Due to the low flow velocity, a laminar flow is achieved and air bubbles can rise.

In one advantageous embodiment of the measuring arrangement, the measurement channel is arranged below the main channel and branches off from the main channel in an inlet region in the region of the inlet. Already due to the fact that the measurement channel is arranged below the main channel, largely foam-free milk is conducted into the measurement channel. Preferably, in the inlet region, a screen is arranged between the main channel and the measurement channel in order to keep impurities, such as residues of straw for example, away from the measurement region.

While the main channel has a substantially constant cross-section between the inlet and the outlet, in another advantageous embodiment of the measuring arrangement the measurement channel is provided with a widening cross-section between the inlet and the outlet. In this widening cross-section, milk with a low foam content can collect in the lower region for the measurement, whereas foam formed by rising air bubbles can collect in the upper part of the cross-section.

In another advantageous embodiment of the measuring arrangement, the measurement channel, at the end thereof opposite the inlet region, opens with at least one run-off into the main channel. During or after a measurement, the milk runs off through the at least one run-off and ensures that at all times in the measurement region it is possible to analyse milk of a composition that substantially corresponds to the milked milk currently flowing into the inlet.

Preferably, at least two run-offs are arranged one above the other, a lower run-off for a liquid milk phase and an upper run-off for milk foam. The lower run-off preferably has a small cross-section (compared to the main channel), so that only a low speed of movement occurs in the measurement channel and in particular in the measurement region. The measurement can thus be carried out with a low foam content and with little milk movements and thus with low turbulence, which is advantageously reflected in a noise-free and reproducible measurement. The milk foam can be conducted out of the measurement channel and back into the main channel through the upper run-off, without disrupting the measurement.

In addition to the lower run-off, an additional lower run-off may be provided, which can be closed by way of a valve arrangement. The permanently open run-off enables a permanent low milk flow in order to achieve only little movement of the milk in the measurement channel and in the measurement region during the measurement. The opening of the additional lower run-off, which can be controlled by way of the valve arrangement, enables accelerated emptying of the measurement channel and, by virtue of a possible larger opening cross-section, prevents any clogging of the run-off.

In an alternative measuring arrangement, a single run-off is provided on the measurement channel, which single run-off can be closed by way of a valve arrangement. The single run-off may have a cross-section comparable to that of the main channel. In this embodiment, a measurement is carried out not on a continuous milk stream, but rather on a portion of milk that is completely stopped in its flow movement for a certain time. To this end, at the start of a measurement cycle, the valve arrangement is first opened so that milk that is currently being milked also flows through the measurement channel. The valve arrangement is then closed so that the milk accumulates in the measurement channel and thus in the measurement region. A certain waiting time is observed, during which the milk in the measurement region comes to rest and air bubbles rise therein. After this waiting time, the optical measurement is carried out, whereupon, on completion of the measurement, the valve arrangement is opened in order to empty the measurement channel and to be able to fill it again with milk that is currently being milked.

In another advantageous embodiment of the measuring arrangement, the optical measuring device is arranged in the region of at least one light in-coupling window and at least one light out-coupling window on the measurement channel. The two windows serve for radiating light into the measurement region and respectively for out-coupling transmitted and/or reflected light for measurement and evaluation. Instead of separate in-coupling and out-coupling windows, use can also be made of a measurement cuvette that is transparent on all sides.

A measurement can be carried out in a transmission geometry if light is radiated in on one side of the measuring device and is out-coupled on an opposite side. For measurement in a reflection geometry, the radiation and out-coupling take place from one side.

In another advantageous embodiment of the measuring arrangement, at least one sensor is arranged in the measurement channel. The sensor may be, for example, a temperature sensor for detecting a temperature of the milk during the optical measurement. The measured optical properties of the milk may have a temperature dependency, which by virtue of the measured temperature can be taken into account in the evaluation. By way of example, a conductivity or impedance sensor may also be provided, for example in the form of electrodes. By measuring the conductivity or impedance, information about properties of the measured milk can be obtained to support the optical measurements.

BRIEF DESCRIPTION OF THE DRAWINGS

The invention will be explained in greater detail below on the basis of exemplary embodiments and with the aid of figures. In the figures.

DETAILED DESCRIPTION OF THE DRAWINGS

Figure 1:
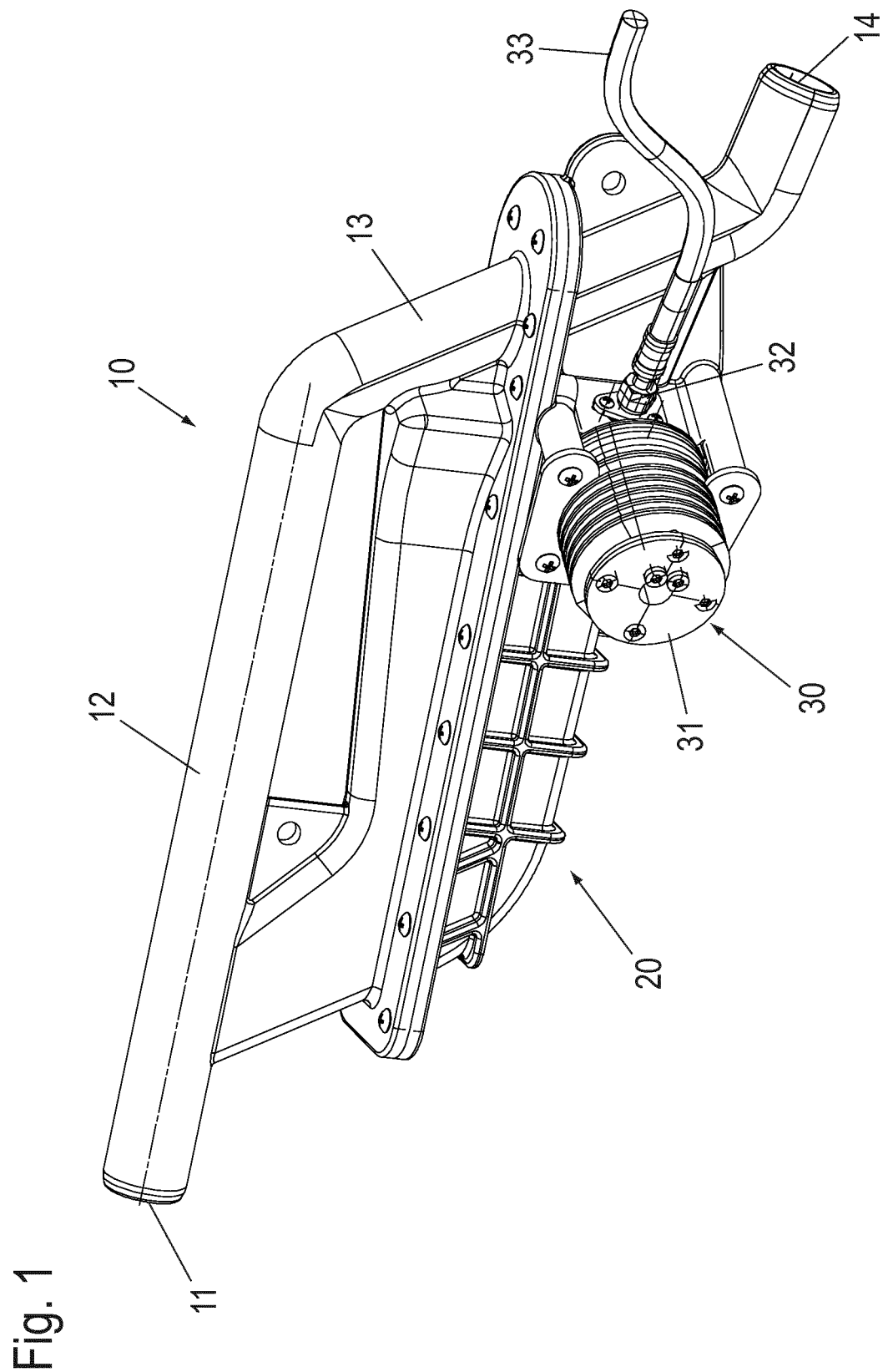
FIG. 1 shows a first exemplary embodiment of a measuring arrangement in an isometric overall view.

FIG. 1 shows, in an isometric oblique view, a first exemplary embodiment of a measuring arrangement for carrying out optical measurements during a milking process.

The measuring arrangement is designed as a one-piece measuring cell, which can be inserted in a milk line.

A main channel 10 is formed, which has an inlet 11 for connection to the milk line and through which the milked milk enters the measuring arrangement.

The main channel 10 can be divided into two portions, a first portion 12, which in an installed orientation extends substantially horizontally or in a slightly inclined manner, and a second portion 13, which is inclined downwards. Arranged at the end of the second portion 13 is an outlet 14, from which the milk that has flowed into the inlet 11 exits again. The measuring arrangement can thus be inserted in a milk line. Due to the compact design of the measuring arrangement, it is easily possible to arrange the measuring arrangement in a milk line that is connected to a teat cup, thereby enabling a measurement on individual quarters. The cross-section (which here is round) of the main channel 10 is substantially constant over the length thereof.

In addition to the main channel 10, the measuring arrangement has a measurement channel 20, which is connected to the main channel 10 after the inlet 11 thereof in order to receive and convey onwards some of the milk flowing into the inlet 11. The measurement channel 20 is additionally connected to the main channel 10 in the region of the second portion 13 in order to feed milk that has flowed through the measurement channel 20 back to the main channel 10 and thus to the outlet 14. Details regarding the connection of the measurement channel 20 to the main channel 10 will be further explained in connection with FIGS. 2 and 3 below.

Adjacent to the transition region to the second portion 13 of the main channel 10, an optical measuring device 30 is mounted on the measurement channel 20 externally on a housing of the measurement channel 20. The measuring device 30 comprises a light in-coupling 31, by means of which light can be radiated into the interior of the measurement channel 20 through a window (not visible here). Light reflected or scattered therein emerges from the housing of the measurement channel 20 through another window (likewise not visible here) and is picked up by a light out-coupling 32 and is coupled into a light guide 33.

The light guide 33 leads to a spectrometer (not shown here), by which properties of the out-coupled light, in particular the intensity thereof, are determined at one or more particular frequencies and in particular at a plurality of frequencies varying over a range. Such spectrometers for wavelengths that may lie in the visible frequency range (VIS), in the infrared frequency range (IR or NIR) or in the ultraviolet frequency range (UV) are known in principle and will not be described in detail at this point. The light source used within the light in-coupling 31 is adapted to the wavelength range to be measured and may comprise, for example, an incandescent bulb or a light-emitting diode as the light source.

Figure 4:
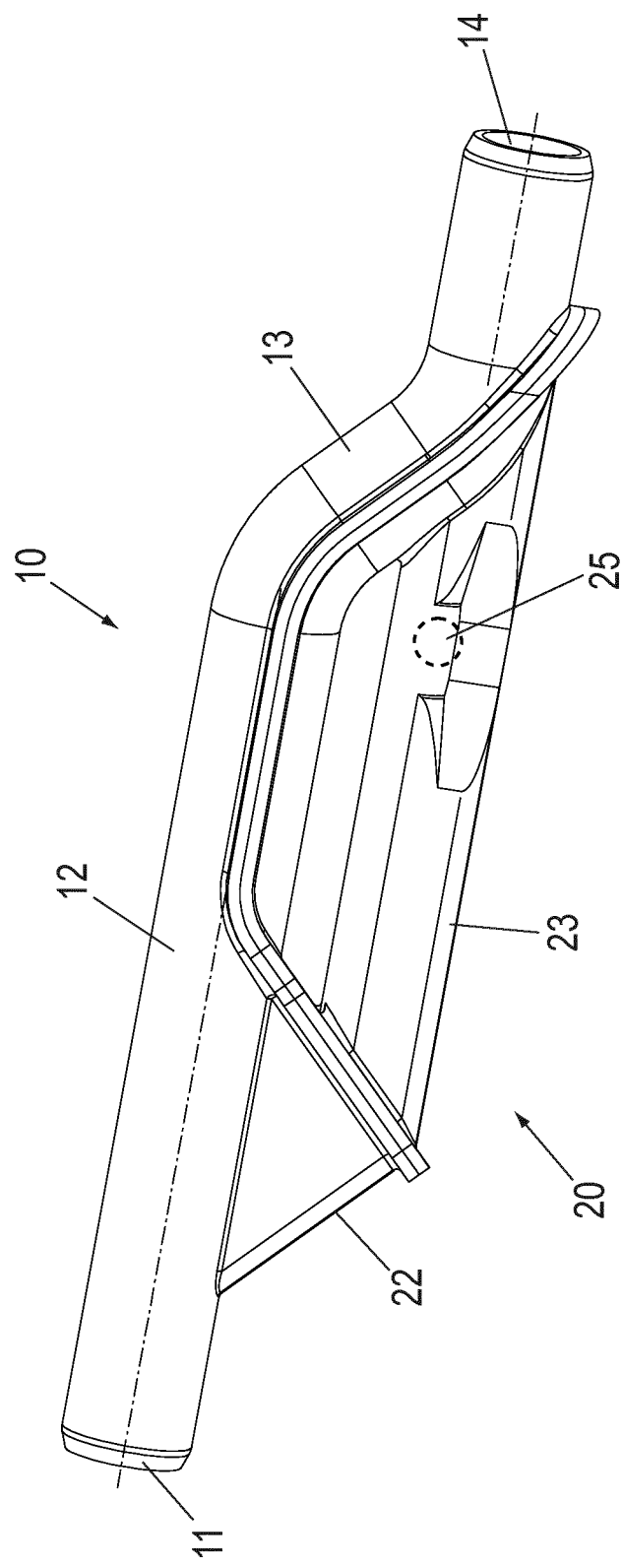
FIG. 4 shows a second exemplary embodiment of a measuring arrangement in an isometric overall view.
Figure 5:
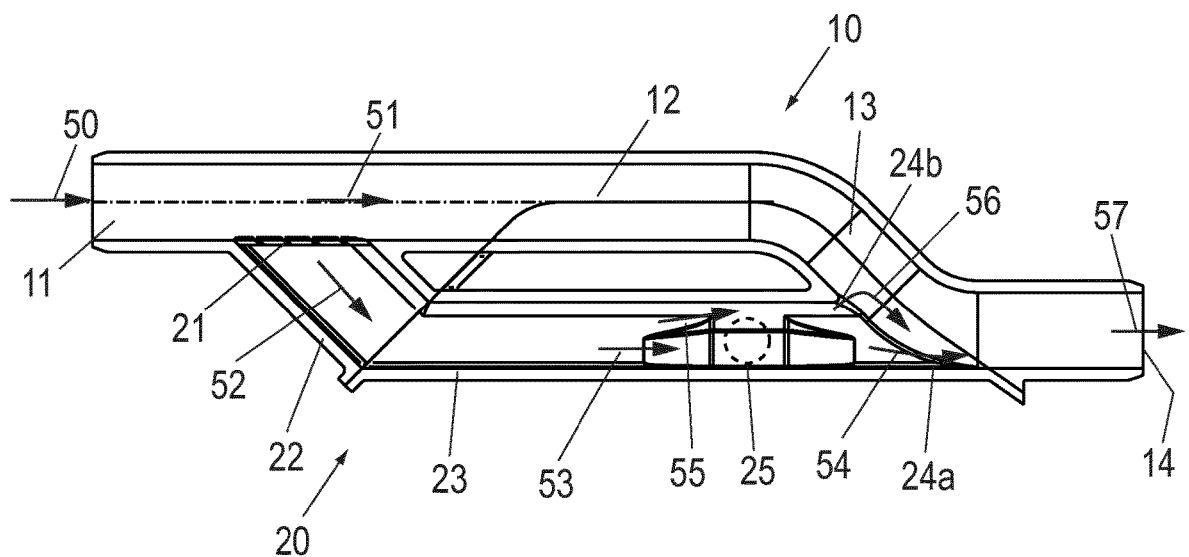
FIGS. 5, 6 each show a schematic sectional illustration of the measuring arrangement of the second exemplary embodiment.
Figure 6:
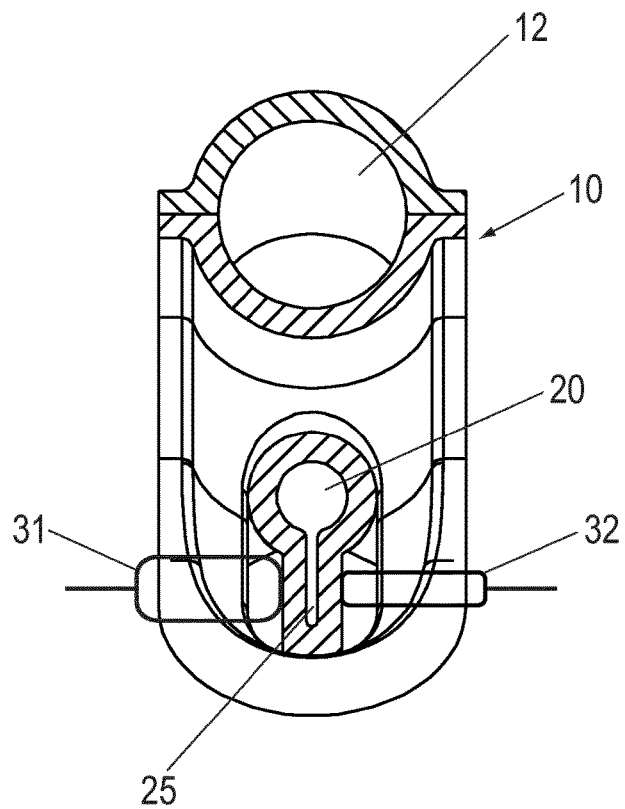

In the example shown, the optical measurement takes place in a reflection geometry, which means that the light in-coupling 31 and the light out-coupling 32 are positioned on the same side of the measurement channel 20. It will be noted that the measurement principle shown in FIG. 1 can in principle be used also in a transmission geometry, in which the light in-coupling 31 and the light out-coupling 32 are positioned on opposite sides of the measurement channel 20. If necessary, the geometry of the measurement channel 20 in the region of the measurement is to be adapted so that the distance to be traversed by the light in the milk is kept so short that a sufficient light intensity can be observed even in transmission. In principle, however, there are no restrictions on using the illustrated measuring device also in a transmission geometry. One exemplary embodiment for a measurement in transmission geometry is shown in FIGS. 4-6. Details regarding the set-up of the measuring device 30 for the reflection measurements shown here are described below in connection with FIG. 3.

Figure 2:
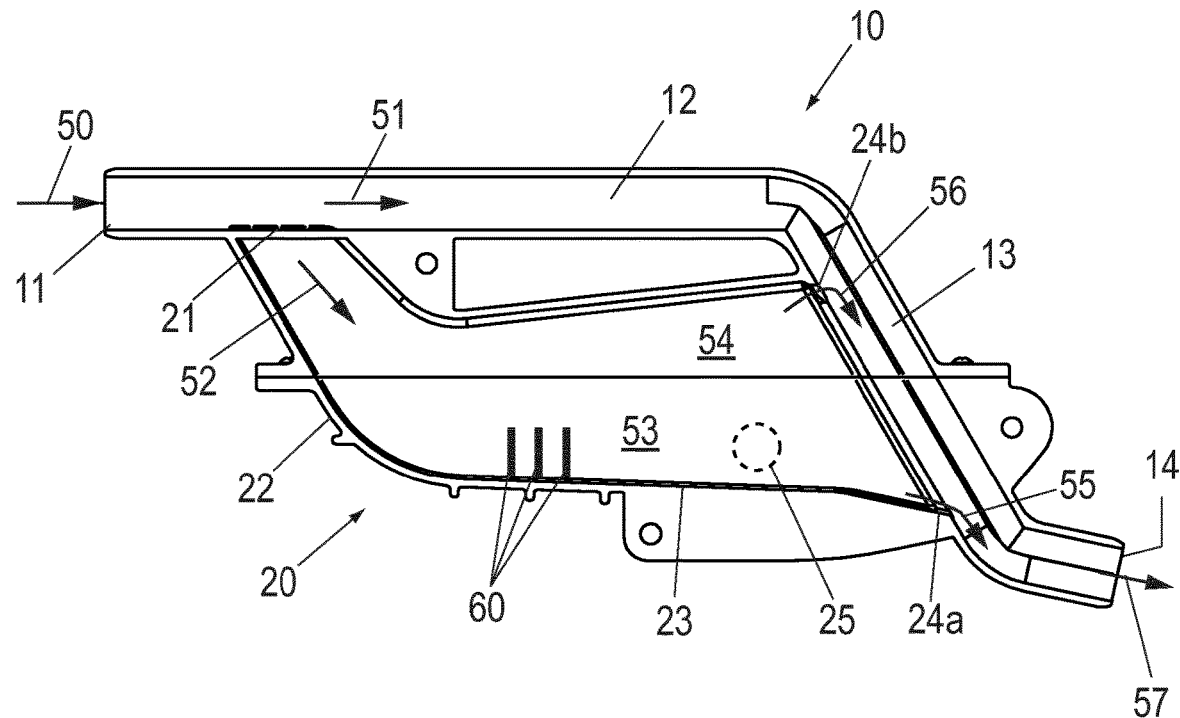
FIGS. 2, 3 each show a schematic sectional illustration of the measuring arrangement of the first exemplary embodiment.

FIG. 2 shows a vertical section through the measuring arrangement shown in FIG. 1. FIG. 2 shows in particular the geometry of the measurement channel 20 and also the connection regions between the main channel 10 and the measurement channel 20.

As already mentioned in connection with FIG. 1, in a region behind the inlet 11, the measurement channel 20 branches off in a downward direction from the main channel 10 in an inlet region 21. A screen can be inserted in this inlet region 21 in order to prevent the ingress of coarser particles, for example residues of straw that were still located on the teat or on the teat cup. The screen additionally reduces the amount of flow entering the measurement channel 20 from the main channel 10. Instead of a screen, one or more suitably small openings may be provided between the main channel 10 and the measurement channel 20, which lead to the same effects.

The measurement channel 20 can also be roughly divided into two portions, a first portion 22, which extends from the inlet region 21 in a manner inclined downwards, and a second portion 23, which is oriented substantially horizontally. Over the course of the measurement channel 20, the cross-section thereof widens continuously. A flow velocity correspondingly decreases continuously. At the side of the second, inclined portion 13 of the main channel 10, the height of the measurement channel 20 extends approximately over the entire length of the second portion 13. At this side, the measurement channel 20 is hydraulically connected to the main channel 10 only at two defined points, namely a lower run-off 24a and an upper run-off 24b. These run-offs 24a, b are designed in the form of small bores or channels.

During operation of the measuring arrangement, milk flows into the inlet 11. In the milking process, on account of the pulsation milking process that is usually used and the vacuum applied to the milk lines and thus also to the illustrated measuring arrangement, the milk is moved through the milk line and thus also through the inlet 11 in a pulsating manner at high speed. Due to the high speed and the small cross-section leading to the measurement channel 20 in the inlet region 21, most of the milk remains in the main channel 10 and a relatively small portion enters the measurement channel 20.

An inflowing milk stream 50 therefore splits into a main milk stream 51 and a measurement milk stream 52, as symbolized by the flow arrows in FIG. 2. The milk flowing into the measurement channel 20 via the measurement milk stream 52 collects in the widened measurement channel 20. Milk 53 with a low foam content settles in the lower region of the measurement channel 20 in a substantially liquid phase. Any air bubbles still contained in the milk 53 or formed as the latter runs into the measurement channel 20 rise upwards and form milk foam 54, which floats and collects in the upper region of the measurement channel 20.

The milk 53 with the low foam content flows off through the lower run-off 24a. A resulting milk stream 55 running off is indicated in FIG. 2. Based on the cross-sections in the inlet region 21 and of the lower run-off 24a, a certain level is established in the measurement channel 20 for the milk 53 with a low foam content.

The milk foam 54 that is formed can leave the measurement channel 20 through the upper run-off 24b as milk foam 56 running off and is thus fed back to the main channel 10. The milk stream 55 flowing out of the measurement channel 20 from the lower run-off 24a likewise mixes with the milk in the main channel 10, which then leaves the measuring arrangement through the outlet 14 as an outflowing milk stream 57.

Due to the smaller cross-sections of the inlet region 21 and of the lower run-off 24a compared to the main channel 10, the flow rate of the milk 53 in the measurement channel 20 is low. In conjunction with the large cross-section of the measurement channel 20, very little movement of the milk 53 in the measurement channel 20 and in particular in a measurement region 25 (symbolized by a circle shown in dashed line in FIG. 2) is achieved.

The optical measurement is carried out in this measurement region 25. The measurement can thus be carried out with a low foam content and little milk movements and thus low turbulence, which is advantageously reflected in a noise-free and reproducible measurement.

Figure 3:
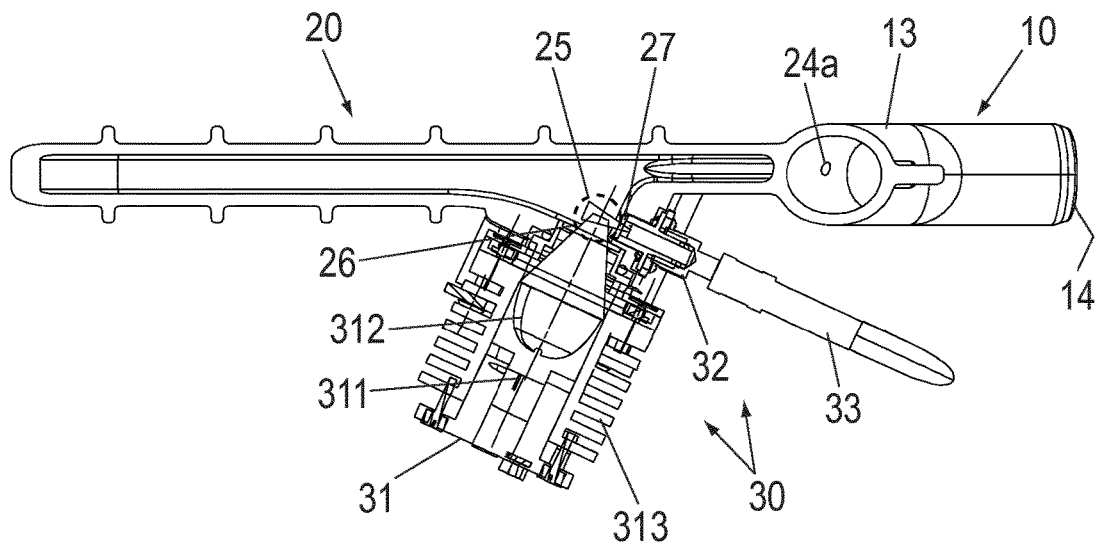

FIG. 3 shows a horizontal cross-section through the measuring arrangement shown in FIGS. 1 and 2 in the area of the measurement region 25. FIG. 3 shows that the measurement channel 20 is widened to the side in the measurement region, in order to offer sufficient space for the reflection measurement. A light in-coupling window 26 and a light out-coupling window 27 are arranged on the measurement channel 20 and are positioned substantially at right angles to one another.

The light in-coupling 31 of the measuring device 30 is positioned in front of the light in-coupling window 26 and is held for example with the aid of a screw-on flange. The light in-coupling 31 comprises a light source 311, for example a light-emitting diode. Light emitted from the latter is bundled with the aid of a collimator 312 and enters the measurement channel 20 through the light in-coupling window 26. The light in-coupling 31 is equipped with cooling ribs 313 in order to be able to dissipate the heat that is generated during operation of the light source 311.

Light scattered by the milk 53 in the measurement region 25 partially exits through the light out-coupling window 27 and enters the light guide 33 of the light out-coupling 32 for further evaluation in the aforementioned spectrometer.

In the exemplary embodiment shown, sensors 60 are additionally arranged in the measurement channel 20. Among the sensors 60 there may be, for example, a temperature sensor for detecting a temperature of the milk during the optical measurement. The measured optical properties of the milk may have a temperature dependency, which by virtue of the measured temperature can be taken into account in the evaluation. By way of example, a conductivity or impedance sensor may also be provided, for example in the form of electrodes. By measuring the conductivity or impedance, information about properties of the measured milk can be obtained to support the optical measurements.

In the exemplary embodiment shown in FIGS. 1-3, on completion of a milking process, the measurement channel 20 is emptied in that the milk 53 runs out of the measurement channel 20 through the lower run-off 24a. During the measurement, the constant run-off through the lower run-off 24a ensures that at all times in the measurement region it is possible to analyse milk of a composition that substantially corresponds to the milked milk currently flowing into the inlet 11.

FIGS. 4-6 show a second exemplary embodiment of a measuring arrangement. FIG. 4 shows the measuring arrangement in an isometric drawing. FIG. 5 shows the measuring arrangement in a manner comparable to FIG. 2 in a vertical section. Finally, FIG. 6 shows the measuring arrangement in a section transverse to the milk flow direction. In these figures, as in all the other figures, the same reference signs denote elements that are the same or that have the same effect as in the previously described figures.

In terms of the basic set-up, the measuring arrangement of FIGS. 4-6 corresponds to that of the first exemplary embodiment. Reference is hereby expressly made to the description concerning FIGS. 1-3. In particular, also in this exemplary embodiment, the milk path is separated after the inlet 11 into a main channel 10 and a measurement channel 20, in which the measurement region 25 is located. The text that follows primarily addresses the differences between the exemplary embodiments.

The measuring arrangement of the second exemplary embodiment, in contrast to that of the first exemplary embodiment, is designed for a measurement in transmission geometry. To this end, the measurement channel 20 tapers in the measurement region 25 to a thickness of a few millimetres. At this layer thickness, light can be shone through milk located in the measurement region 25.

The tapering of the measurement channel 20 is clearly visible in the sectional illustration of FIG. 6. The tapering is limited to a lower part of the cross-section, which is keyhole-shaped, so that rising air bubbles can collect as milk foam in the upper, wider part of the cross-section and the lower part of the cross-section is as far as possible free of air bubbles. In this figure, a light in-coupling 31 and a light out-coupling 32 of the measuring arrangement are shown schematically. The light used for the measurement radiates through the milk in the measurement region 25.

Figure 7:
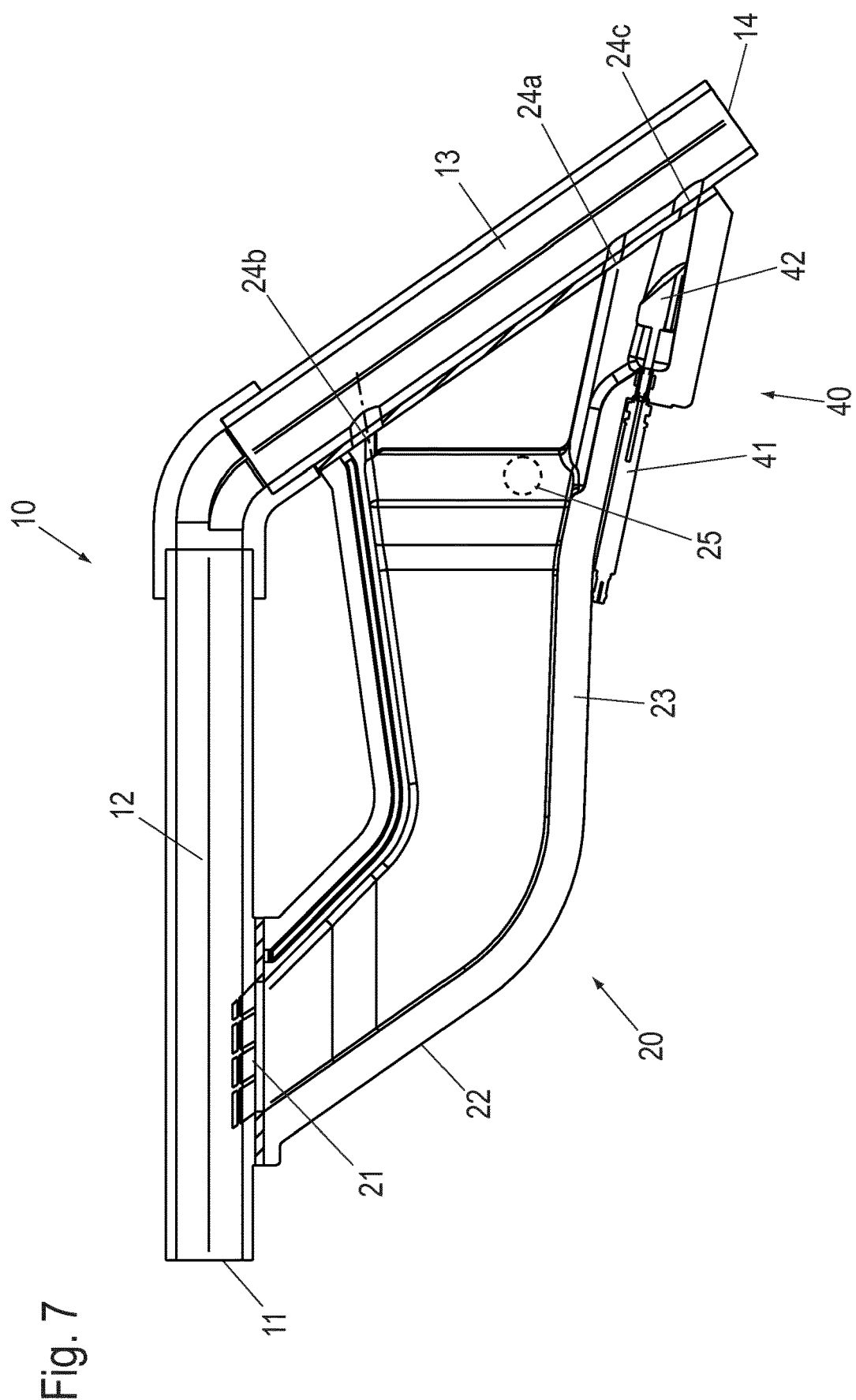
FIG. 7 shows a third exemplary embodiment of a measuring arrangement in a schematic sectional illustration.

FIG. 7 shows, in an illustration comparable to that of FIG. 2, a third exemplary embodiment of a measuring arrangement.

In terms of the basic set-up, the measuring arrangement of FIG. 7 also corresponds to that of the first exemplary embodiment. Once again, the text that follows primarily addresses the differences.

In the exemplary embodiment of FIG. 7, two lower run-offs 24a, 24c are provided one above the other in the lower region of the measurement channel 20, namely an additional lower run-off 24c besides the lower run-off 24a. As in the first exemplary embodiment, the run-off 24a is permanently open and enables a permanent low milk flow in order on the one hand to achieve only little movement of the milk 53 in the measurement channel 20 in the measurement region 25 during the measurement and on the other hand to empty the measurement channel on completion of the measurement in each case.

The additional lower run-off 24c is designed as a closable run-off that can be actuated. To this end, a valve arrangement 40 is provided, in which an actuator 41, for example a pneumatic cylinder, has a closure element 42 at the end of a piston rod. By way of the actuator 31, the closure element 42 can be pressed onto the further lower run-off 24c in order to close the latter.

The valve arrangement 40 can be used to empty the measurement channel 20 in an accelerated manner on completion of a measurement. Since this possibility is provided, the diameter of the permanently open lower run-off 24a can be selected to be so small that there is particularly little movement of the milk 53 during the measurement process. The larger additional lower run-off 24c also prevents clogging of the measuring arrangement by dirt particles.

Another difference in the exemplary embodiment of FIG. 7 lies in the construction of the housing of the measuring arrangement. In the first exemplary embodiment of FIGS. 1-3, the housing that forms the main channel 10 and the measurement channel 20 is constructed in two parts, the housing having an upper housing part and a lower housing part.

In the exemplary embodiment of FIG. 7, the housing is likewise constructed in two parts, but in this case the housing halves are separated in a vertical plane and not in a horizontal plane.

Figure 8:
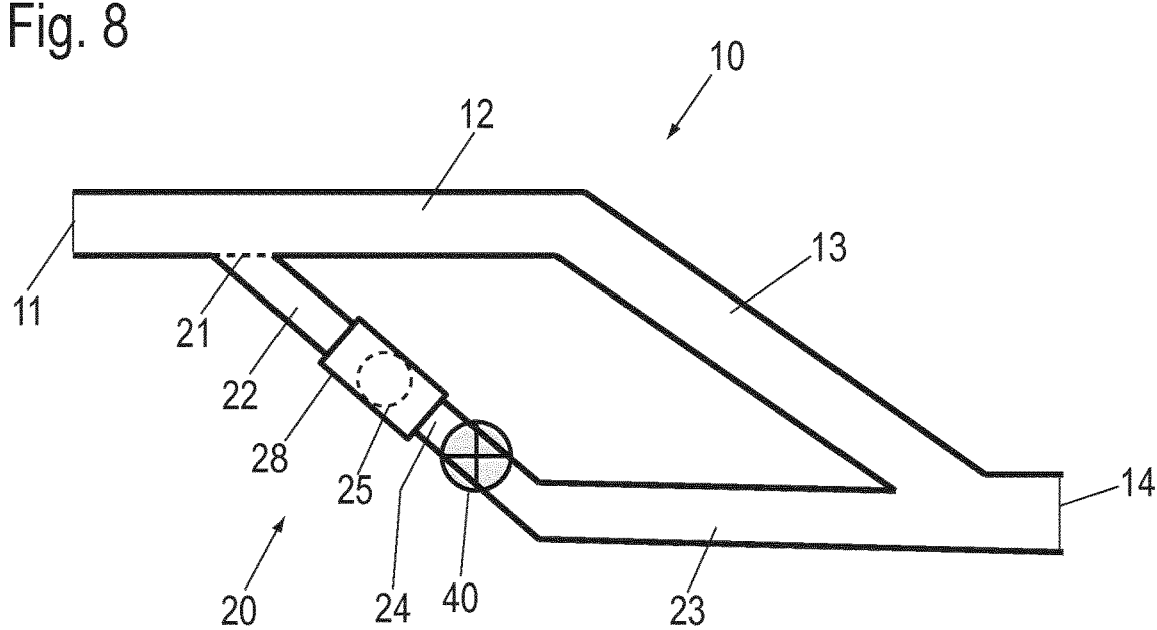
FIG. 8 shows a fourth exemplary embodiment of a measuring arrangement in an isometric overall view.
Figure 9:
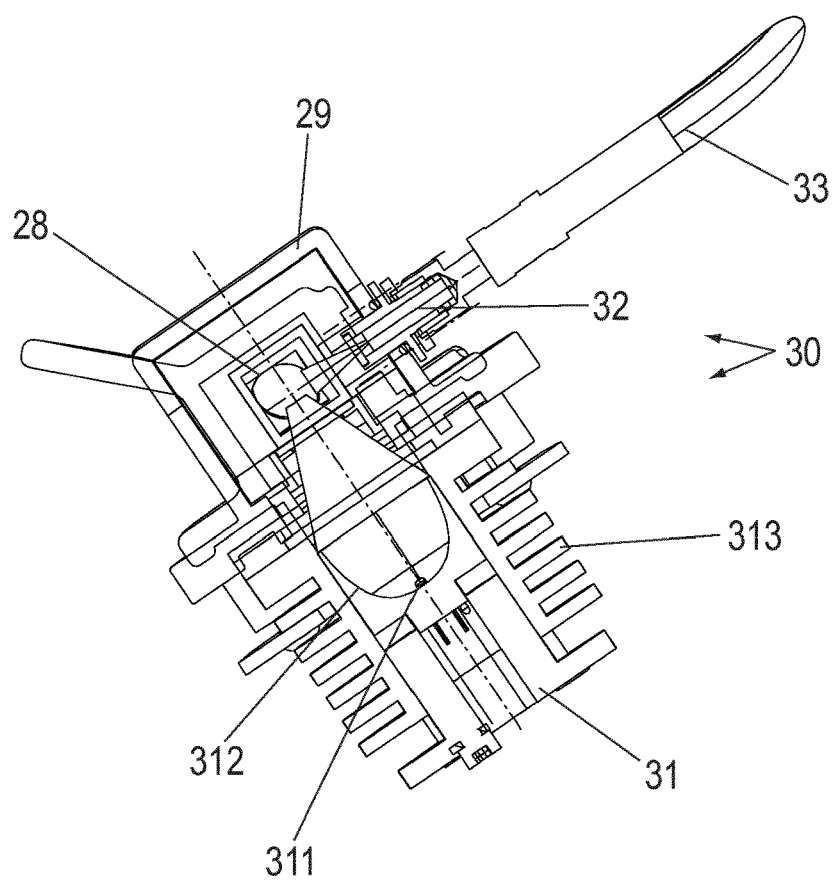
FIG. 9 shows a schematic sectional illustration of the measuring arrangement of the fourth exemplary embodiment.

FIGS. 8 and 9 show another exemplary embodiment of a measuring arrangement, by which optical measurements can be carried out inline during the milking process. FIG. 8 shows the measuring arrangement in an isometric overall view. FIG. 9 shows a section through a measurement region 25.

As in the previously described exemplary embodiments, a main channel 10 is formed with an inlet 11 and a first horizontal portion 12 and an inclined second portion 13, which opens into an outlet 14.

Behind the inlet 11, a measurement channel 20 branches off in the downward direction from the main channel 10, once again in an inlet region (not visible in the figures). The measurement channel 20 opens into a measurement cuvette 28, within which the measuring region 25 is located. A run-off 24 of the measurement cuvette 28 is connected to the second portion 13 of the main channel 10 via a valve arrangement 40. The valve arrangement 40 may comprise, for example, a pneumatically actuated straight-way valve with a vacuum unit as actuator.

The measuring arrangements of the first three illustrated exemplary embodiments enable measurements on a portion of the milk in the measurement channel that flows continuously but at a low flow rate in the measurement region 25. Due to the low and non-turbulent flow, a foam content is reliably separated out and air bubbles can rise prior to the measurement.

In contrast, in the exemplary embodiment of FIGS. 8 and 9, a measurement is carried out not on a continuous milk stream, but rather on a portion of milk that is completely stopped in its flow movement for a certain time. To this end, at the start of a measurement cycle, the valve arrangement 40 is first opened so that some of the milk that is currently being milked also flows through the measurement channel 20. The valve arrangement 40 is then closed so that milk accumulates in the measurement channel 20 and thus in the measurement cuvette 28. A certain waiting time is observed in order to give the milk in the measurement cuvette 28 time to come to rest. During this waiting time, air bubbles can also rise. After the waiting time, the optical measurement is carried out, whereupon, on completion of the measurement, the valve arrangement 40 is opened in order to empty the measurement cuvette 28 and the measurement channel 20 again and to fill them with milk that is currently being milked.

FIG. 9 shows a section through the measurement cuvette 28 with the measuring device 30 of the exemplary embodiment shown in FIG. 8 arranged in this region.

Here, the measurement cuvette 28, for example a glass cuvette, is arranged in a measurement chamber 29, to which the measuring device is attached. The milk to be measured flows into the measurement cuvette 28 and remains in the measurement cuvette 28 during the measurement. The measurement cuvette 28 is transparent so that no separate light in-coupling windows or light out-coupling windows are necessary.

The light in-coupling 31 once again comprises a light source 311 and a collimator 312 for radiating light in bundled form into the measurement cuvette 28. Cooling ribs 313, which serve to cool the light source 311, are formed on the light in-coupling 31. With regard to the light sources and the wavelength ranges used, reference is made to the first exemplary embodiment.

The light out-coupling 32 with its light guide 33 is arranged perpendicular to the direction in which the light is radiated in. The measurement thus takes place in reflection geometry.

As shown in FIG. 8, the light that is radiated in also radiates through the measurement cuvette 28. It would therefore be possible, as an alternative or in addition, to arrange a further light out-coupling on the side of the measurement chamber 29 located opposite the light in-coupling 31 for a measurement in transmission geometry.

The invention claimed is:

1. An optical milk measuring apparatus comprising:
a main milk channel having an inlet and an outlet; and
a milk measurement channel in fluid communication with the main milk channel between the inlet and the outlet, defining a measurement region, and having a milk flow rate that is less than a milk flow rate in the main milk channel;
wherein the milk measurement channel defines a first lower liquid milk phase run-off and a second liquid milk phase run-off and each have a flow cross-section that is substantially less than a flow cross-section of the milk measurement channel.

2. The optical milk measuring apparatus of claim 1, wherein the milk measurement channel is disposed below the main channel.

3. The optical milk measuring apparatus of claim 1, and further comprising:
a screen is disposed between the inlet and the milk measurement channel.

4. The optical milk measuring apparatus of claim 1, wherein the main milk channel has a substantially constant cross-sectional flow area between the inlet and the outlet.

5. The optical milk measuring apparatus of claim 1, wherein the milk measurement channel defines a cross-sectional area that increases from an inlet region toward the measurement region.

6. The optical milk measuring apparatus of claim 1, and further comprising:
a valve in fluid communication with the second lower liquid milk phase run-off, and movable between a closed position and an open position.

7. The optical milk measuring apparatus of claim 1, wherein the milk measurement channel defines a light-in window and a light-out window, and the optical milk measuring apparatus further comprises:
an optical sensor in communication with the light-in window and the light-out window.

8. The optical milk measuring apparatus of claim 1, wherein the milk measurement channel includes a substantially transparent cuvette; and
the optical milk measurement device further comprises:
an optical sensor in communication with the milk measurement channel through the substantially transparent cuvette.

9. The optical milk measuring apparatus of claim 1, and further comprising:
an optical milk sensor having a light-in coupling and a light-out coupling in releasable engagement with the milk measurement channel.

10. The optical milk measuring apparatus of claim 1, and further comprising:
a sensor in communication with the measurement flow channel, and the sensor is selected from the group comprising:
a temperature sensor;
a conductance sensor; and
an impedance sensor.

11. An optical milk measuring apparatus comprising:
a main milk channel having an inlet and an outlet;
a milk measurement channel in fluid communication with the main milk channel between the inlet and the outlet, defining a measurement region, and having a milk flow rate that is less than a milk flow rate in the main milk channel; and
an optical milk sensor in communication with the milk measurement channel, a light-in coupling and a light-out coupling, and the light-in coupling and the light-out coupling are disposed on the same side of the milk measurement channel in a reflection geometry with one another.

12. The optical milk measuring apparatus of claim 11, wherein the milk measurement channel defines a run-off in fluid communication with the main milk channel.

13. The optical milk measuring apparatus of claim 11, wherein the milk measurement channel defines a lower liquid milk phase run-off and an upper milk foam run-off.

14. The optical milk measuring apparatus of claim 11, wherein the milk measurement channel defines a first lower liquid milk phase run-off and a second liquid milk phase run-off each have a flow cross-section that is substantially less than a flow cross-section of the milk measurement channel.

15. The optical milk measuring apparatus of claim 11, wherein the milk measurement channel defines a milk run-off, and the optical milk measuring apparatus further comprises:
a valve disposed in fluid communication with the milk run-off, and movable between a closed position and an open position.

16. The optical milk measuring apparatus of claim 11, wherein the milk measurement channel defines a milk run-off with a milk flow cross-section that is substantially equal to a milk flow cross-section of the main milk channel.

17. The optical milk measuring apparatus of claim 11, wherein the milk measurement channel is disposed below the main channel.

18. The optical milk measuring apparatus of claim 11, and further comprising:
a screen is disposed between the inlet and the milk measurement channel.

19. The optical milk measuring apparatus of claim 11, wherein the main milk channel has a substantially constant cross-sectional flow area between the inlet and the outlet.

20. The optical milk measuring apparatus of claim 11, wherein the milk measurement channel defines a cross-sectional area that increases from an inlet region toward the measurement region.

21. The optical milk measuring apparatus of claim 11, wherein the milk measurement channel defines a first lower liquid milk phase run-off and a second lower liquid milk phase run-off; and the optical milk measuring apparatus further comprises:
a valve in fluid communication with the second lower liquid milk phase run-off, and movable between a closed position and an open position.

22. The optical milk measuring apparatus of claim 11, wherein the milk measurement channel defines a milk run-off, and the optical milk measuring apparatus further comprises:

a valve disposed in fluid communication with the milk run-off, and movable between a closed position and an open position.

23. The optical milk measuring apparatus of claim 11, wherein the milk measurement channel defines a light-in window and a light-out window, and the optical milk measuring apparatus further comprises:

an optical sensor in communication with the light-in window and the light-out window.

24. The optical milk measuring apparatus of claim 11, wherein the milk measurement channel includes a substantially transparent cuvette; and wherein the optical milk measurement sensor is in communication with the milk measurement channel through the substantially transparent cuvette.

* * * * *